United States Patent
Joensuu

(10) Patent No.: US 9,157,773 B2
(45) Date of Patent: Oct. 13, 2015

(54) SENSOR VALIDATION METHOD, PATIENT MONITOR, PHYSIOLOGICAL SENSOR, AND COMPUTER PROGRAM PRODUCT FOR A PATIENT MONITOR

(75) Inventor: Heikki Joensuu, Vantaa (FI)

(73) Assignee: General Electric Company, Schenectady, NY (US)

(*) Notice: Subject to any disclaimer, the term of this patent is extended or adjusted under 35 U.S.C. 154(b) by 467 days.

(21) Appl. No.: 13/484,387

(22) Filed: May 31, 2012

(65) Prior Publication Data

US 2013/0325388 A1 Dec. 5, 2013

(51) Int. Cl.
*G01D 18/00* (2006.01)
*A61B 5/00* (2006.01)
*A61B 5/1455* (2006.01)
*G06F 19/00* (2011.01)

(52) U.S. Cl.
CPC ............ *G01D 18/008* (2013.01); *A61B 5/1455* (2013.01); *A61B 5/7221* (2013.01); *G06F 19/3412* (2013.01)

(58) Field of Classification Search
CPC .................. A61B 5/00; A61B 5/1495; A61B 2560/0276; A61B 2562/085
USPC .......... 702/104; 600/300, 301, 323, 324, 485; 705/14.66
See application file for complete search history.

(56) References Cited

U.S. PATENT DOCUMENTS

| | | | | |
|---|---|---|---|---|
| 7,048,687 B1* | 5/2006 | Reuss et al. | .................... | 600/300 |
| 7,248,910 B2* | 7/2007 | Li et al. | ......................... | 600/323 |
| 7,809,419 B2 | 10/2010 | Fein et al. | | |
| 7,894,849 B2* | 2/2011 | Kass et al. | ................. | 455/550.1 |
| 7,949,380 B2 | 5/2011 | Fein et al. | | |
| 8,200,320 B2* | 6/2012 | Kovacs | ......................... | 600/513 |
| 8,652,126 B2* | 2/2014 | Rantala | .......................... | 606/34 |
| 2004/0267103 A1* | 12/2004 | Li et al. | ......................... | 600/323 |
| 2006/0161054 A1* | 7/2006 | Reuss et al. | .................... | 600/300 |
| 2007/0208233 A1* | 9/2007 | Kovacs | ......................... | 600/300 |
| 2012/0179066 A1* | 7/2012 | Hsu et al. | ...................... | 600/586 |
| 2014/0343375 A1* | 11/2014 | Mannheimer et al. | ........ | 600/301 |

* cited by examiner

*Primary Examiner* — Carol S Tsai
(74) *Attorney, Agent, or Firm* — Andrus Intellectual Property Law, LLP

(57) ABSTRACT

In order to increase sensor manufacturing yield without compromising patient safety, at least one first value is determined respectively for at least one sensor feature parameter indicative of characteristics of a physiological sensor and the determined value(s) is/are stored in a predefined memory location prior to use of a physiological sensor. In response to the physiological sensor being connected to a patient monitor, at least one second value is defined respectively for the at least one sensor feature parameter and the at least one first value of each of the at least one sensor feature parameter is retrieved from the predefined memory location. Each of the at least one second value is compared with respective at least one first value and a decision is made, based on the comparison, on the acceptance of the physiological sensor.

14 Claims, 3 Drawing Sheets

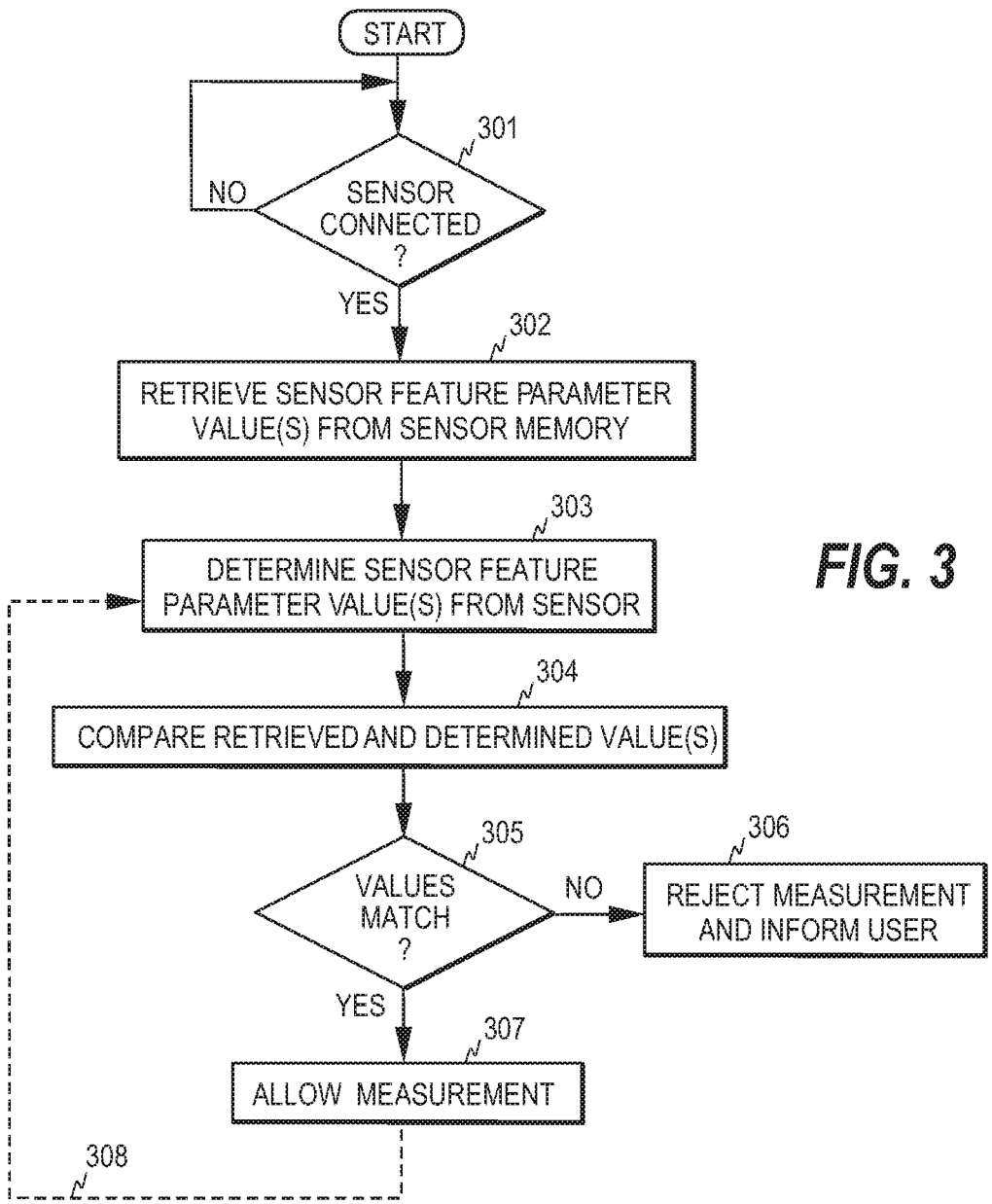

SENSOR VALIDATION METHOD, PATIENT MONITOR, PHYSIOLOGICAL SENSOR, AND COMPUTER PROGRAM PRODUCT FOR A PATIENT MONITOR

BACKGROUND OF THE INVENTION

This disclosure relates generally to patient monitors and physiological sensors used for acquiring electrophysiological signals from a subject/patient. More particularly, the disclosure relates to validation of a physiological sensor connected to a patient monitor.

A prerequisite of patient care is that accurate and reliable measurements can be made from the patient to evaluate the patient's state. Since a patient monitor connected to a sensor may perform rather complex calculations based on the physiological signals acquired through the sensor and since the results obtained may depend on a variety of parameters related to the sensor, it is important that the sensor fulfills certain quality standards and is thus authorized to be used in the patient monitor for the measurement in question. The use of aged, damaged or low quality sensors may lead to inaccurate and/or unreliable results, which may in turn contribute to incorrect medical decisions and even risk patient safety.

In terms of patient safety, die use of non-authentic unauthorized and/or counterfeited sensors is also to be prevented, since the cooperation of such sensors with the patient monitor is not tested and the sensors therefore involve the same risks as authentic but aged or low quality sensors.

It is therefore common practice to provide a sensor/monitor system with a detection mechanism that detects aged and/or unauthorized sensors, or with a mechanism that tends to improve the performance level of the sensor. The solutions may be classified into different categories according to the type of data stored in the sensor and according to the way in which data stored in sensor memory is employed. Typically, the content of the sensor memory is used by a monitor algorithm to make the measurement more accurate. For this, the sensor memory may hold sensor parameters that are relevant to the measurement. The sensor parameters are typically variables that the patient monitor is incapable of measuring, such as LED wavelengths. The sensor memory may also hold operating parameters that prevent the use of the sensor outside a safe operating range. A further solution is to record other information related to the use of the sensor into the sensor memory, such as total usage time, manufacturer identification, expiration data, or warranty date of the sensor. A still further solution is to use the sensor memory content to upgrade the software in the oximeter monitor itself in order to improve the accuracy and/or performance or to update the functionality of the patient monitor.

Although current solutions can prevent the use of sensors that may compromise patient safety, these solutions cannot achieve their objectives without detracting from the yield of the manufacturing process. In the manufacturing phase, several parameters are currently measured from the sensors manufactured. These parameters are used in quality control to monitor the quality of the manufactured sensors and to identify the sensors that may not function properly in the monitor. Due to the inherent variability of the manufacturing process, which inevitably results in variability in sensor parameter values, wide enough acceptance criteria are generally necessary for the sensor parameters to ensure an adequate process yield. This is significant especially when manufacturing disposable sensors, due to the tighter cost requirements compared to reusable products. However, as patient safety cannot be compromised, the acceptance criteria have to be tight enough to ensure patient safety. That is, the requirement of patient safety is contradictory to the pursuit of high manufacturing yield.

Consequently, the requirement of patient safety translates into the above-mentioned tight acceptance criteria for the sensor, which in turn detracts from the yield of the manufacturing process and thus also increases the product costs.

BRIEF DESCRIPTION OF THE INVENTION

The above-mentioned problem is addressed herein which will be comprehended from the following specification. In the disclosed solution, a parameter measured from the sensor is used to evaluate whether the physical sensor originates from its true manufacturing process intact and without excessive decline in sensor quality. This enables improved manufacturing yield and prevents the use of unauthorized and aged or low quality sensors in the patient monitor in order not to risk patient safety.

In an embodiment, a method for validating a physiological sensor connected to a patient monitor comprises determining at least one first value respectively for at least one sensor feature parameter indicative of characteristics of a physiological sensor and storing the at least one first value of each of the at least one sensor feature parameter in a predefined memory location, wherein the determining and storing are performed prior to use of the physiological sensor. The method further comprises defining, in response to the physiological sensor being connected to a patient monitor, at least one second value respectively for the at least one sensor feature parameter and retrieving the at least one first value of each of the at least one sensor feature parameter from the predefined memory location. The method also comprises comparing each of the at least one second value with respective at least one first value and deciding, based on the comparing, on acceptance of the physiological sensor.

In another embodiment, a patient monitor for monitoring a subject comprises a data retrieval unit configured to retrieve at least one first value respectively for at least one sensor feature parameter from a predefined memory location, wherein the at least one sensor feature parameter is indicative of characteristics of a physiological sensor connected to the patient monitor and a sensor feature determination unit configured to determine at least one second value respectively for the at least one sensor feature parameter from the physiological sensor connected to the patient monitor. The patient monitor further comprises a comparison unit configured to compare the at least one second value with respective at least one first value and a decision-making unit configured to make a decision on acceptance of the sensor, wherein the decision-making unit is responsive to the comparison unit.

In a further embodiment, a physiological sensor attachable to a subject for acquiring a physiological measurement signal from the subject comprises a sensor element unit configured to output an electrophysiological signal, a sensor memory storing at least one first value for a sensor feature parameter indicative of characteristics of the sensor, and a memory access interface for enabling a patient monitor operably connected to the sensor to retrieve the at least one first value for comparison with at least one second value of the sensor feature parameter, wherein the at least one second value of the sensor feature parameter is determined by the patient monitor from the sensor when the sensor is connected to the patient monitor.

In a still further embodiment, a computer program product for validating a physiological sensor connected to a patient monitor comprises a first program product portion configured to retrieve at least one first value respectively for at least one sensor feature parameter from a predefined memory location, wherein the at least one sensor feature parameter is indicative of characteristics of a physiological sensor connected to the patient monitor and a second program product portion configured to determine at least one second value respectively for the at least one sensor feature parameter from the physiological sensor connected to the patient monitor. The computer program product further comprises a third program product portion configured to compare the at least one second value with respective at least one first value and a fourth program product portion configured to make a decision on acceptance of the sensor, wherein the fourth program product portion is responsive to the third program product portion.

Various other features, objects, and advantages of the invention will be made apparent to those skilled in the art from the following detailed description and accompanying drawings.

BRIEF DESCRIPTION OF THE DRAWINGS

FIGS. 2 and 3 illustrate an embodiment of the sensor validation mechanism;

DETAILED DESCRIPTION OF THE INVENTION

Figure 1:
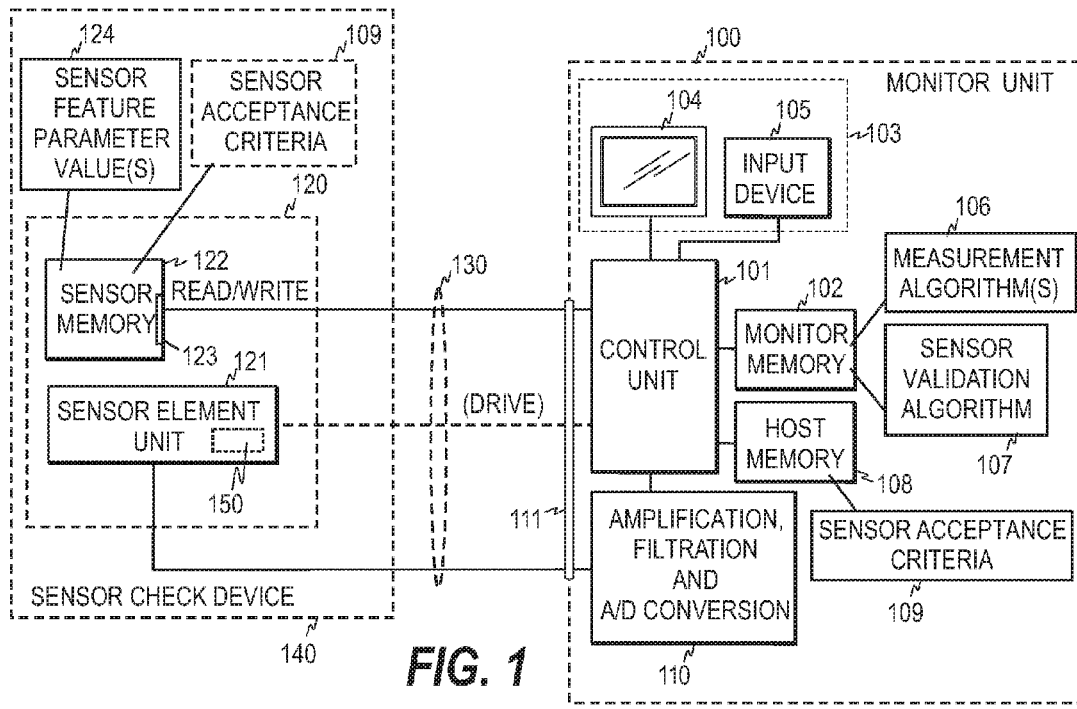
FIG. 1 is a block diagram illustrating an embodiment of a patient monitor system.

FIG. 1 illustrates one embodiment of a sensor and monitor system that is configured to detect whether or not a sensor unit connected to a monitor unit is acceptable. The sensor system of FIG. 1 comprises a monitor unit 100 and a sensor unit 120 attachable to a subject (not shown). The sensor unit 120 is normally connected to the monitor unit 100 through a cable 130, but the connection may also be wireless. It is to be noted that the system is here discussed with respect to one monitor unit 100 and one sensor unit 120 connected to the monitor unit. However, the entire system typically includes several sensor units 120 and one or more monitor units 100.

The monitor unit 100 may be conceived to comprise three basic elements: a computerized control and processing unit 101, a memory 102 for the control and processing unit, and a user interface 103, which typically comprises a display 104 and one or more user input devices 105.

A reception branch 110 of the monitor unit is adapted to receive electrophysiological signals from the sensor. The reception branch typically comprises an input amplifier, a filter, and an A/D converter (not shown). The digitized signal output from the A/D converter is supplied to the control and processing unit 101, which processes the signal data and displays the analysis results on the screen of the display. The memory of the control and processing unit holds the measurement algorithm(s) 106 needed to process the data received from the sensor unit.

The sensor unit of FIG. 1 comprises a sensor element unit 121 and a sensor memory 122. The sensor element unit may comprise an array of light sources combined with at least one photo detector or an array of electrodes that may be attached onto the skin of the subject. The sensor memory 122 may be a generic memory from which the monitor may read data and into which the monitor may write data through a memory access interface 123. The sensor memory may thus be a plain (non-volatile) memory with no customized areas/parts, associated intelligence, or data processing capability. The memory may be, for example, an EEPROM or an EPROM memory. The memory holds one or more sensor-specific values 124 for a sensor feature parameter measured from the sensor prior to the commissioning of the sensor. The sensor feature parameter is a parameter which is indicative of a given feature or the operation of the sensor and which may be used as an evaluation tool for evaluating whether the physical sensor originates from its true manufacturing process intact and without excessive decline in sensor quality. The manufacturing process causes variation in values of the sensor feature parameter, i.e. the parameter value differs significantly in different sensors.

However, the parameter is preferably such that it is rather stable in the sense that the operating conditions do not have a significant effect on the parameter value. As discussed below, in case of an optical sensor the sensor feature parameter may represent, for example, the ratio (rCTR) of two current transfer ratios (CTRs) of the sensor.

The memory 102 of the control and processing unit further holds a sensor validation algorithm 107 that is executed by the control and processing unit when a sensor unit 120 is connected to the monitor unit 100.

The monitor unit 100 may further be provided with a host memory 108 which is here presented as a separate memory unit but which may also be a memory area of the monitor memory 102. The host memory may contain acceptance criteria 109 for the sensor feature parameter, and possibly also other parameters/variables used by the sensor validation algorithm when validating a sensor connected to the patient monitor. For example, the acceptance criteria may include one or more parameters indicative of the acceptable value range for the sensor feature parameter. Since several types of sensors may be connected to the patient monitor, the host memory may include acceptance criteria for different types of sensors.

In another embodiment, the acceptance criteria 109, and possible also other sensor validation parameters needed by algorithm 107, may be stored in the sensor memory 122. Thus, in this embodiment the sensor validation algorithm 107 may obtain all the variables needed for the validation of the sensor from the sensor memory and there is no need to store this data in the monitor.

In a further embodiment, the sensor system may also comprise a sensor check device 140, which is a device to which the sensor unit 120 may be connected to aid the measurement of the sensor feature parameters. For example, the device may be configured to direct the light beams of a reflectance sensor to the photo detector.

FIGS. 2 and 3 illustrate an embodiment of the sensor validation method. FIG. 2 illustrates the steps carried out before the sensor is taken into use, while FIG. 3 illustrates the steps carried out by the control and processing unit 101 of the patient monitor when a sensor is connected to the monitor.

The steps carried out in the manufacturing phase of the sensor include the determination of one or more sensor feature parameter values, thereby to obtain at least one first value for the sensor feature parameter (step 201). The first value(s), which act(s) as a "fingerprint" of the sensor is/are stored into the sensor memory (step 202). As mentioned above, in case of an optical sensor the sensor feature parameter may be, for example, the ratio of the current transfer ratios (rCTR). CTR indicates the ratio of the detector output current to the LED input current for a LED/detector pair when the input current is supplied to the LED. As all the LEDs of a sensor have a certain CTR and as the CTR varies due to the variability in the manufacturing process, CTR may be used as a "fingerprint" that identifies the sensor in question. However, as the absolute value of CTR is sensitive to the distance of the LED from the detector, the ratio of CTRs is more stable than plain CTR, as the LEDs are very close to each other on the sensor substrate. Consequently, one or more CTR ratios may be determined in step 201 and stored in step 202 in sensor memory. The number of ratios determined and stored may depend on the number of wavelengths (LEDs) in the sensor. The CTR may be measured when the sensor is off the measurement site (finger or ear) or in sensor calibration mode of the monitor. Steps 201 and 202 may be carried out by any suitable measuring device used in the manufacturing phase of the sensor to monitor the quality of the sensor. This measuring device may be, for example, a patient monitor or a device that comprises the measuring units of a patient monitor, since the patient monitor is configured to determine the sensor feature parameter in order to validate the sensor. As indicated above, the acceptance criteria 109 and other possible parameters/variables of the validation algorithm may also be determined in step 201 and stored in the sensor memory in step 202.

With reference to FIG. 3, during use the control and processing unit of the patient monitor constantly monitors whether or not a sensor is connected to the monitor unit (step 301). Upon detecting that a sensor is connected to the monitor unit (step 301/yes), the control and processing unit retrieves the sensor feature parameter value(s) from the sensor memory (step 302), thereby to obtain at least one first value for the sensor feature parameter. The control and processing unit then determines (step 303) the sensor feature parameter value(s) from the sensor, thereby to obtain at least one second value for the sensor feature parameter. That is, in step 303 the control and processing unit measures the value(s) similarly as the value(s) is/are measured in step 201. The control and processing unit then compares the first and second value(s) with each other in step 304 and decides in step 305, whether the measured value(s) match with the stored value(s). If this is the case, measurement is allowed (step 307). In the opposite case, the measurement is rejected (step 306), since it is then likely that the sensor is either aged or not from an authorized manufacturing process, and may therefore pose a risk to patient safety. In one embodiment, the sensor is checked only at the beginning of each measurement session. However, in another embodiment the above operation may continue as a background process during the actual measurement. This is illustrated as a dotted arrow 308 in the figure. The above steps help to detect if the performance of the sensor has degraded substantially or if the sensor is counterfeited in a manner that leaves the memory content and determined parameter value(s) inconsistent with each other.

In one embodiment, the validation process may decide, at step 307, whether the content of the sensor memory and/or the host memory is to be updated. That is, the first value(s) and/or the sensor acceptance criteria may be updated based on the determined sensor feature parameter value(s). In a further embodiment, the validation process may write, at step 306, a reject code into the sensor memory or delete/erase the sensor memory to ensure that the sensor is removed from use.

Figure 4:
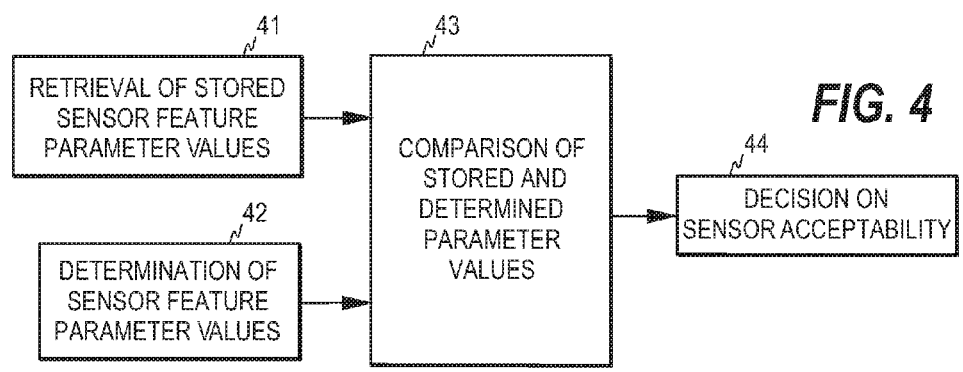
FIG. 4 illustrates an example of the functional units of the patient monitor in terms of sensor validation.

The control and processing unit, which is adapted to execute the sensor validation algorithm, may thus be seen, in terms of the sensor validation, as an entity of different operational modules or units, as is illustrated in FIG. 4. A data retrieval unit 41 is configured to retrieve the stored value(s), i.e. the first value(s), of the sensor feature parameter in response to the connection of the sensor to the monitor, while a sensor feature determination unit 42 is configured to measure the value(s) of the sensor feature parameter from the connected sensor, thereby to obtain at least one second value of the sensor feature parameter. A comparison unit 43 is configured to compare the stored and measured value(s) to determine whether the values match with each other, and a decision-making unit 44 is configured to make decision on the acceptability of the sensor and thus also on the permission/prohibition of the use of the sensor. Depending on the location of the sensor acceptance criteria, unit 41 and/or 43 may retrieve the said data.

In the disclosed solution, sensor feature parameter values are used in a novel manner to improve the yield of sensor manufacturing process without compromising patient safety. The sensor feature parameter may be a parameter that is measured during normal measurement mode of the monitor, such as forward voltage discussed below in connection with FIG. 5. In this way, no additional hardware or software is needed in the monitor to determine the parameter value(s) from the sensor, cf. step 303. The parameter is preferably also such that the manufacturing process causes substantial variation in the parameter values, which ensures that the memory content will match with the specific sensor components only and makes it difficult to counterfeit a sensor so that the components, such as LEDs, selected for the sensor happen to yield a sensor feature parameter value that matches the content of the sensor memory. The acceptable value range stored in the system may be specific to the sensor concerned. The range may depend, for example, on the value(s) of the sensor feature parameter determined in step 201. Due to this, the manufacturing yield will be improved, since the acceptable value range, i.e. the safety margin needed to ensure patient safety, may now be set on a sensor-by-sensor basis rather than using safety margins common to all sensors of the same type, and since the operation of the monitor may be tuned according to the actual sensor condition.

Figure 5:
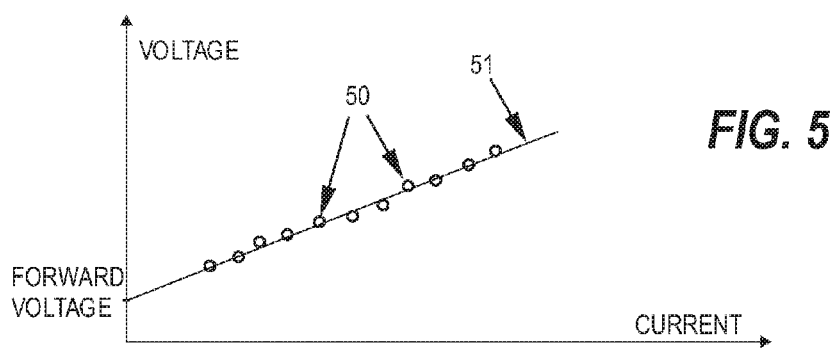
FIG. 5 illustrates the determination of one sensor feature parameter.

Another parameter that may be used for validating an optical sensor, provided that the monitor is equipped with the necessary measurement hardware, is forward voltage (also termed forward voltage drop), which is the voltage drop across a LED when current is flowing through the LED. FIG. 5 illustrates one embodiment of the determination of forward voltage. In this embodiment, different currents are supplied to a LED and the corresponding voltages are measured. As a result, several data points 50 are obtained. Based on the data points a straight line 51 is fitted through the data points. The voltage value that the line approaches when current approaches zero then indicates the forward voltage. Thus, in this embodiment, the monitor is configured to measure the voltage over and the current through desired LEDs.

A further possible feature parameter is a temperature difference determined based on the resistance of a thermistor used in the sensor. That is, the behavior of a thermistor as part of the thermodynamical system of the sensor can be utilized to validate the sensor. The resistance of the sensor thermistor is measured in an initial "cool" state and then in a "warm" state after the sensor has been used so that stable state has been reached. If the sensor or the thermistor is not damaged, the temperature change, i.e. the temperature difference between "warm" and "cool" states, of the sensor should be substantially the same as initially measured in the manufacturing phase.

One or more first and second values may be determined for one sensor feature parameter, such as the ratio of CTRs. If only one first and one second value is determined, the comparison carried out by the monitor is straightforward. However, if several first and second values are determined, such as CTR ratios for several LED pairs, the validation criteria may vary. For example, a separate criterion may be set for each ratio or a common criterion may be set for the sum of the differences of the corresponding first (stored) and second (determined) values. The values of some components, such as LEDs with specific wavelengths, may also be more important than those of other components.

It is also possible to use several sensor feature parameters, such as two parameters. In this embodiment, the acceptance criteria may require, for example, that each sensor feature parameter is to meet the acceptance criteria before the use of the sensor is accepted. If it is detected that two feature parameters correspond to the original condition accurately enough, it is even more likely that the sensor is an original sensor that has not suffered from substantial quality degradation. In case of several sensor feature parameters, only part of the parameters may be used to validate the sensor. The parameters used may depend on the type of the measurement. Different sensor feature parameters may also be determined in different measurement phases (at sensor connection and during the actual measurement). The comparison between stored and measured/determined value(s) may also involve calculating a measure that indicates how far the sensor is from a rejection limit.

In a further embodiment, the sensor may include a dummy element, which is an element that does not relate to the actual measurement, such as a resistor connected to an additional wire or in parallel to a LED. In the manufacturing phase, a dummy element with a given electrical value is selected for the sensor and the value is stored in the sensor memory. The selection may be made from among dummy elements having a variety of electrical values. When the sensor is used, the electrical value is determined and compared with the stored value to validate the sensor. The dummy element is denoted with reference number 150 in FIGS. 1 and 6. The dummy element may be used in addition to a sensor feature parameter indicative of sensor quality degradation.

Figure 6:
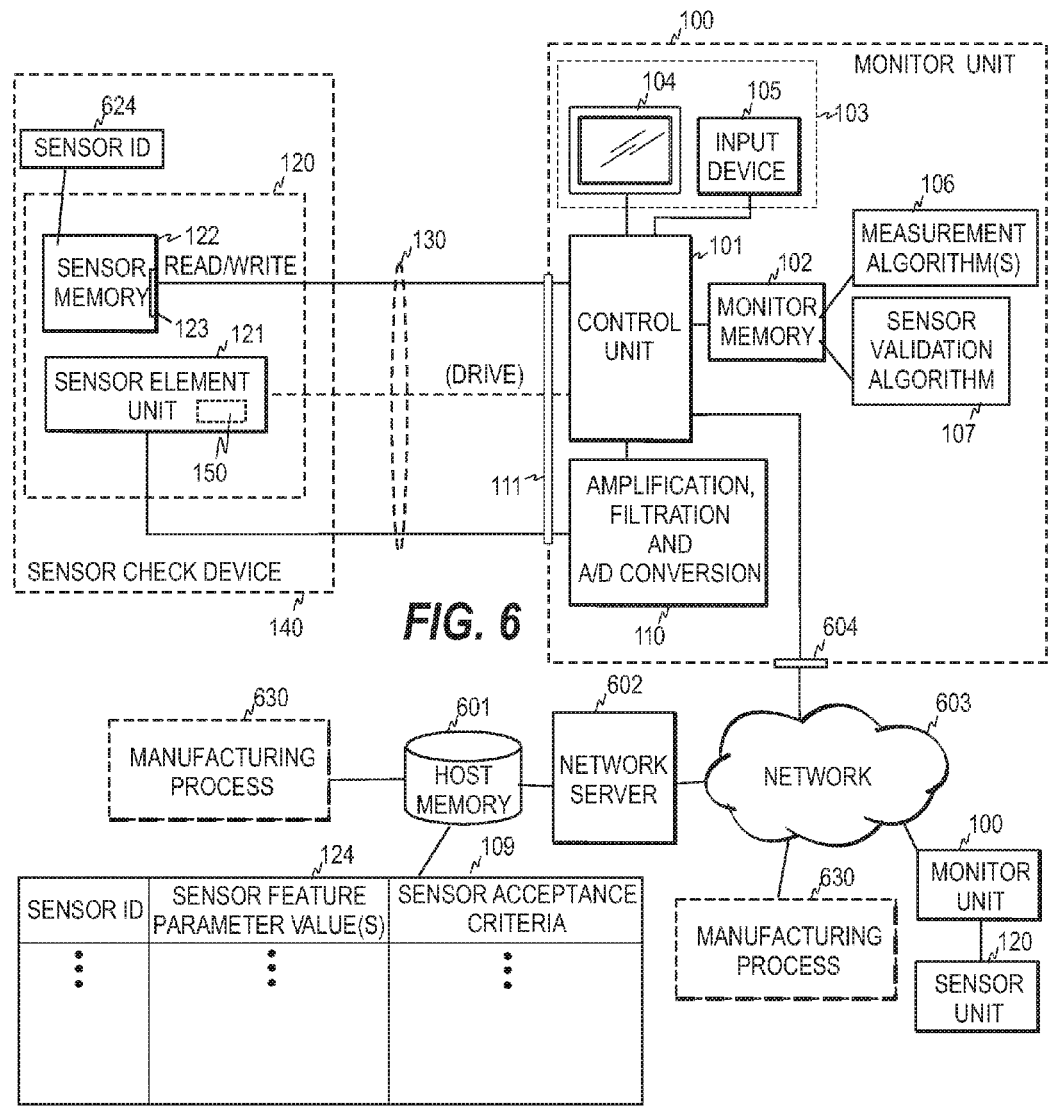
FIG. 6 illustrates another embodiment of the patient monitor system.

In the above embodiments, the necessary information for the sensor validation is in the sensor or in the patient monitor, or distributed between the sensor and the monitor. However, at least part of the necessary information may also be stored in an external host memory that may be accessed by several monitors through the network. As is shown in FIG. 6, the host memory 601 may be in conjunction with a network element, such as a database server 602, through which the host memory may be accessed by a plurality of monitor units connected to the same network 603 as the server. The network may be a local area network, such as a hospital network, a wide area network, or the Internet, for example. Each monitor unit is provided with a network interface 604 and a suitable transmission protocol for reading from the host memory 601. In these embodiments, the sensor memory 122 may include a sensor identifier 624 that identifies the sensor connected to the patient monitor. Based on the sensor identifier 624, the patient monitor may retrieve the necessary information for the sensor validation, i.e. the first value(s) of the sensor feature parameter(s) and possibly also the acceptance criteria, from the host memory 601. The manufacturing process 630 may store the sensor identifier and the said information in the host memory locally or through the network, depending on the locations of the host memory and the manufacturing process.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for validating a physiological sensor connected to a patient monitor, the method comprising:
   determining at least one first value respectively for at least one sensor feature parameter indicative of operational characteristics of a physiological sensor in measuring physiological signals;
   storing the at least one first value of each of the at least one sensor feature parameter in a predefined memory location, wherein the determining and storing are performed prior to use of the physiological sensor;
   measuring, in response to the physiological sensor being connected to a patient monitor, at least one second value respectively for the at least one sensor feature parameter;
   retrieving the at least one first value of each of the at least one sensor feature parameter from the predefined memory location;
   comparing each of the at least one second value with respective at least one first value; and
   deciding, based on the comparing, on acceptance of the physiological sensor.

2. The method according to claim 1, wherein the storing comprises storing the at least one first value of each of the at least one sensor feature parameter in a predefined memory location, in which the predefined memory location is in a memory of the physiological sensor.

3. The method according to claim 1, wherein the determining and storing are performed in manufacturing phase of the physiological sensor.

4. The method according to claim 2, wherein the deciding comprises;
   allowing use of the connected physiological sensor in the patient monitor when the comparing indicates that the at least one second value fulfills predetermined criteria in relation to the at least one first value; and
   rejecting the use of the connected physiological sensor otherwise.

5. The method according to claim 4, wherein the rejecting includes modifying content of the memory of the physiological sensor, thereby to make the content indicative of a defective sensor.

6. The method according to claim 1, wherein the determining, comprises determining the at least one first value respectively for the at least one sensor feature parameter, wherein the at least one sensor feature parameter represents at least one parameter in a group including a first parameter indicative of ratio of current transfer ratios of two light sources of the physiological sensor, a second parameter indicative of forward voltage of a light, source of the physiological sensor, and a third parameter indicative of a temperature change determined through a thermistor of the physiological sensor.

7. A patient monitor for monitoring, a subject, the patient monitor comprising:
   data retrieval unit configured to retrieve at least one first value respectively for at least one sensor feature parameter fir a physiological sensor connected to the patient monitor from a predefined memory location, wherein the at least one sensor feature parameter is indicative of operational characteristics of the physiological sensor in measuring physiological signals;
   a sensor feature determination unit configured to measure at least one second value respectively for the at least one sensor feature parameter from the physiological sensor connected to the patient monitor;

a comparison unit configured to compare the at least one second value with respective at least one first value; and a decision-making unit configured to make a decision on acceptance of the sensor, wherein the decision-making unit is responsive to the comparison unit.

8. The patient monitor according to claim 7, wherein the decision-making unit is configured to allow use of the connected physiological sensor in the patient monitor when the at least one second value fulfills predetermined criteria in relation to the at least one first value:, and reject the use of the connected physiological sensor in the patient monitor otherwise.

9. The patient monitor according to claim 8, wherein the decision-making unit is further configured to modify content of a memory of the physiological sensor, thereby to make the content indicative of a defective sensor.

10. The patient monitor according to claim 8, wherein the patient monitor is configured to retrieve the predetermined criteria from a predetermined memory location.

11. The patient monitor according to claim 7, wherein the at least one sensor feature parameter represents at least one parameter in a group including a first parameter indicative of ratio of current transfer ratios of two light sources of the physiological sensor, a second parameter indicative of forward voltage of a light source of the physiological sensor, and a third parameter indicative of a temperature change determined through a thermistor of the physiological sensor.

12. A physiological sensor attachable to a subject for acquiring a physiological measurement signal from the subject, the sensor comprising:

a sensor element unit configured to output an electrophysiological signal;

a sensor memory storing at least one first value for a sensor feature parameter indicative of operational characteristics of the sensor in measuring physiological signals; and a memory access interface for enabling a patient monitor operably connected to the sensor to retrieve the at least one first value for comparison with at least one second value of the sensor feature parameter, wherein the at least one second value of the sensor feature parameter is measured by the patient monitor from the sensor when the sensor is connected to the patient monitor.

13. The sensor according to claim 12, wherein the sensor memory further stores predetermined acceptance criteria associated with the sensor feature parameter.

14. A computer program product encoded on a non-transitory computer-readable medium for validating a physiological sensor connected to a patient monitor, the computer program product comprising:

instructions executable to retrieve at least one first value respectively for at least one sensor feature parameter for the physiological sensor from a predefined memory location, wherein the at least one sensor feature parameter is indicative of operational characteristics of the physiological sensor in measuring physiological signals;

instructions executable to measure at least one second value respectively for the at least one sensor feature parameter from the physiological sensor connected to the patient monitor;

instructions executable to compare the at least one second value with respective at least one first value; and instructions executable to make a decision on acceptance of the sensor, wherein the fourth program product portion is responsive to the third program product portion.

* * * * *